US010342490B2

(12) United States Patent
Henderson et al.

(10) Patent No.: US 10,342,490 B2
(45) Date of Patent: Jul. 9, 2019

(54) SIDE-LOADING CONNECTORS WITH INLINE CABLING FOR USE WITH INTRAVASCULAR DEVICES AND ASSOCIATED SYSTEMS AND METHODS

(71) Applicant: KONINKLIJKE PHILIPS N.V., Eindhoven (NL)

(72) Inventors: Eric Henderson, Escondido, CA (US); Katie Keller, San Diego, CA (US); Mark Richardson, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

(21) Appl. No.: 15/749,091

(22) PCT Filed: Jul. 28, 2016

(86) PCT No.: PCT/IB2016/054528
§ 371 (c)(1),
(2) Date: Jan. 30, 2018

(87) PCT Pub. No.: WO2017/021834
PCT Pub. Date: Feb. 9, 2017

(65) Prior Publication Data
US 2018/0220969 A1 Aug. 9, 2018

Related U.S. Application Data

(60) Provisional application No. 62/199,708, filed on Jul. 31, 2015.

(51) Int. Cl.
*H01R 13/625* (2006.01)
*A61B 5/00* (2006.01)
(Continued)

(52) U.S. Cl.
CPC ........ *A61B 5/6851* (2013.01); *A61B 5/02158* (2013.01); *A61B 8/0891* (2013.01);
(Continued)

(58) Field of Classification Search
CPC .................................................... H01R 24/58
(Continued)

(56) References Cited

U.S. PATENT DOCUMENTS 5,931,861 A 8/1999 Werner et al.
2003/0199948 A1 10/2003 Kokones
(Continued)

*Primary Examiner* — Phuong K Dinh

(57) ABSTRACT

Intravascular devices, systems, and methods are disclosed. In some embodiments, side-loading electrical connectors for use with intravascular devices are provided. The side-loading electrical connector has at least one electrical contact configured to interface with an electrical connector of the intravascular device. A first connection piece of the side-loading electrical connector is movable relative to a second connection piece such that in an open position an elongated opening is formed between the first and second connection pieces to facilitate side-loading of the intravascular device into the connector and in the closed position the at least one electrical contact is electrically coupled to the at least one electrical connector of the intravascular device received between the first and second connection pieces and a communication cable extends from the connector in a direction coaxial with or parallel to the longitudinal axis of the intravascular device.

20 Claims, 13 Drawing Sheets

(51) Int. Cl.

| | |
|---|---|
| *A61B 5/0215* | (2006.01) |
| *A61B 8/08* | (2006.01) |
| *A61B 8/00* | (2006.01) |
| A61B 8/12 | (2006.01) |
| H01R 4/48 | (2006.01) |
| H01R 24/58 | (2011.01) |
| H01R 31/06 | (2006.01) |
| A61M 25/00 | (2006.01) |
| A61M 25/09 | (2006.01) |

(52) U.S. Cl.
CPC ............... *A61B 8/445* (2013.01); *A61B 8/12* (2013.01); *A61B 2562/227* (2013.01); *A61M 2025/0002* (2013.01); *A61M 2025/09175* (2013.01); *H01R 4/48* (2013.01); *H01R 24/58* (2013.01); *H01R 31/06* (2013.01); *H01R 2201/12* (2013.01)

(58) Field of Classification Search
USPC ..................... 439/669, 341, 310, 259, 909
See application file for complete search history.

(56) References Cited

U.S. PATENT DOCUMENTS

| | | |
|---|---|---|
| 2004/0186542 A1 | 9/2004 | Van Venrooij |
| 2014/0005536 A1 | 1/2014 | Burkett |
| 2014/0005543 A1 | 1/2014 | Burkett |
| 2014/0005573 A1 | 1/2014 | Burkett |

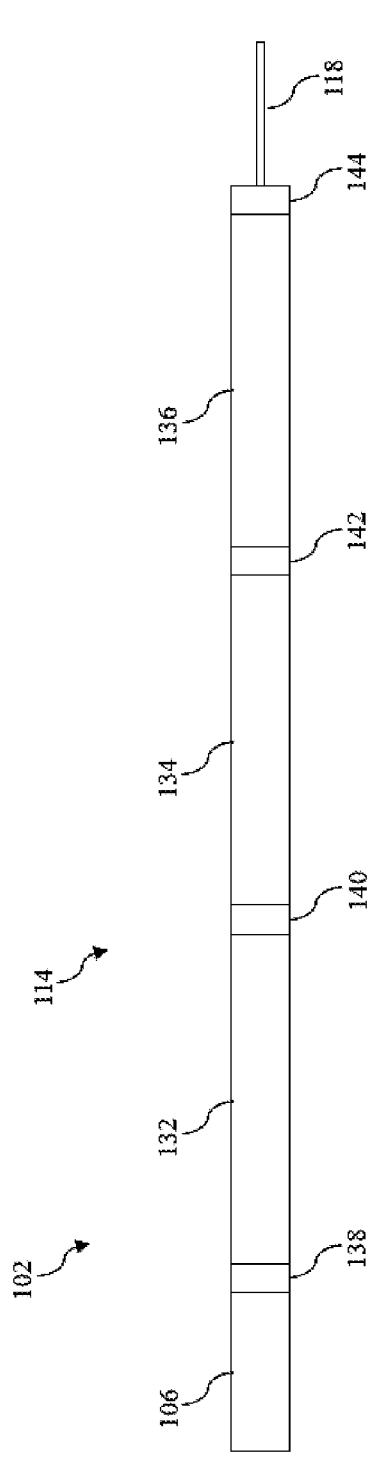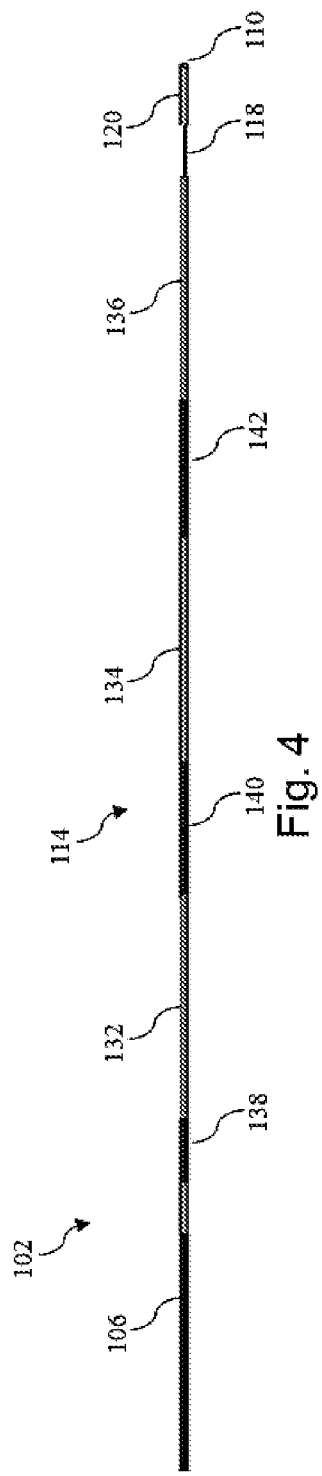

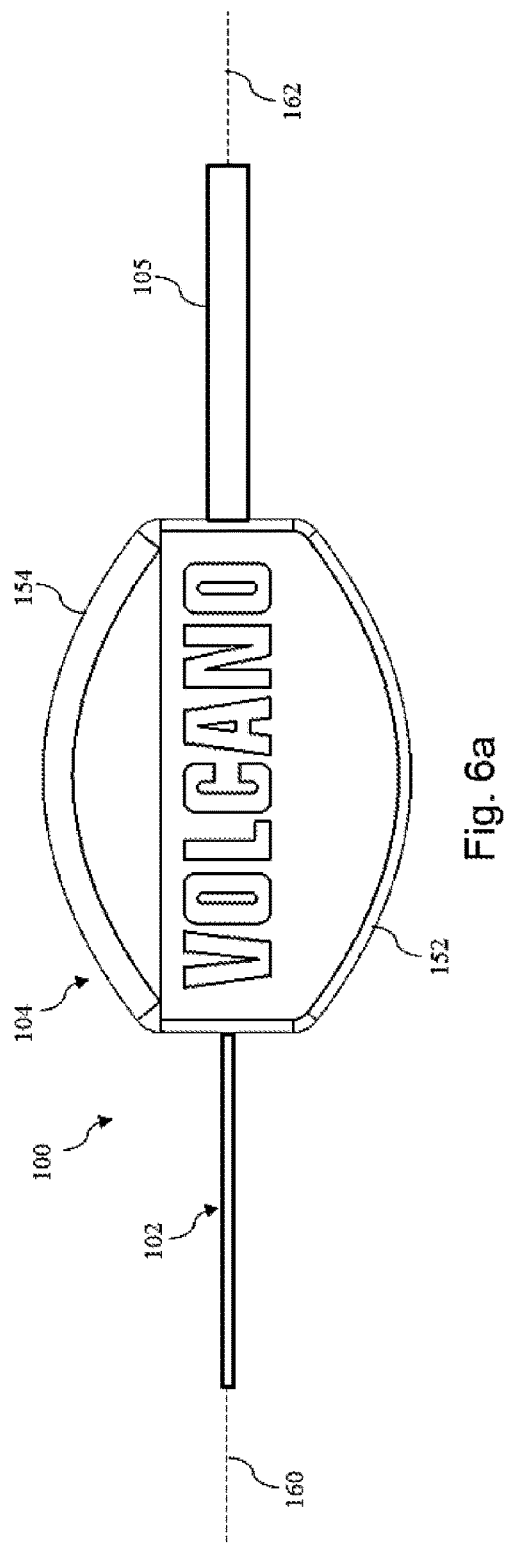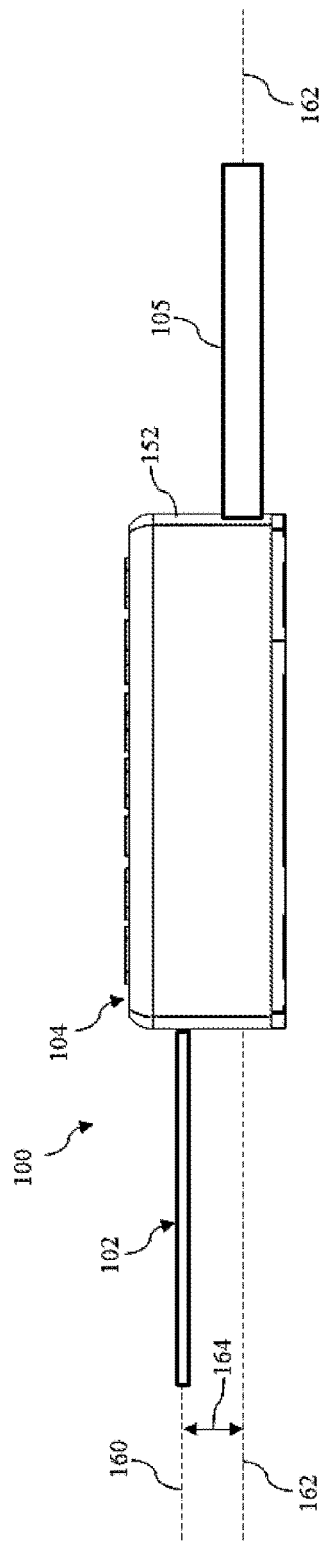

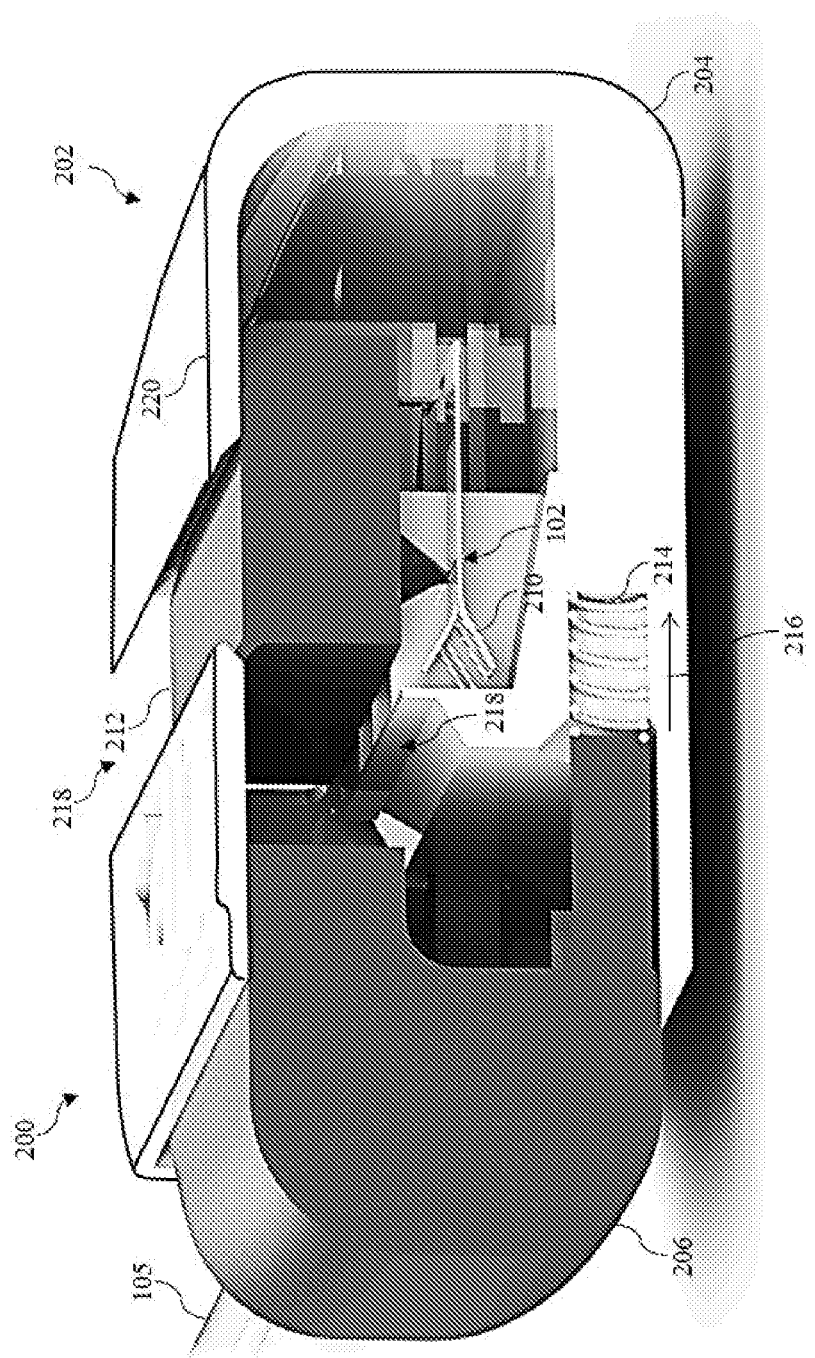

SIDE-LOADING CONNECTORS WITH INLINE CABLING FOR USE WITH INTRAVASCULAR DEVICES AND ASSOCIATED SYSTEMS AND METHODS

CROSS-REFERENCE TO PRIOR APPLICATIONS

This application is the U.S. National Phase application under 35 U.S.C. § 371 of International Application No. PCT/US2016/054528, filed on Jul. 28, 2016, which claims the benefit of U.S. Provisional Patent Application No. 62/199,708 filed on Jul. 31, 2015. These applications are hereby incorporated by reference herein.

TECHNICAL FIELD

The present disclosure relates to intravascular devices, systems, and methods. In some embodiments, the intravascular devices are guidewires that include one or more electronic components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel. To date, guidewires containing pressure sensors or other electronic components have suffered from reduced performance characteristics compared to standard guidewires that do not contain electronic components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Further, due to its small diameter, in many instances the proximal connector portion of the guidewire (i.e., the connector(s) that facilitate communication between the electronic component(s) of the guidewire and an associated controller or processor) can be fragile and prone to kinking, which destroys the functionality of the guidewire. For this reason, surgeons have been reluctant to remove the proximal connector from the guidewire during a procedure for fear of breaking the guidewire when reattaching the proximal connector. However, having the guidewire coupled to the proximal connector further limits the maneuverability and handling of the guidewire.

Accordingly, there remains a need for improved connectors for use with intravascular devices (e.g., catheters and guidewires) that include one or more electronic components.

SUMMARY

Embodiments of the present disclosure are directed to intravascular devices, systems, and methods.

In some embodiments, an intravascular system is provided. The system includes An intravascular system, comprising: an intravascular device having a flexible elongate member having a proximal portion and a distal portion, at least one electronic component secured to the distal portion of the flexible elongate member, and at least one electrical connector secured to the proximal portion of the flexible elongate member, wherein the at least one electrical connector is electrically coupled to the at least one electronic component secured to the distal portion of the flexible elongate member; and a connector for coupling to the proximal portion of the flexible elongate member, the connector having a first connection piece, a second connection piece, wherein the second connection piece is movable relative to the first connection piece between an open position and a closed position, and at least one electrical contact configured to interface with the at least one electrical connector of the intravascular device, wherein in the open position an elongated opening is formed between the first and second connection pieces to facilitate insertion of the at least one electrical connector of the intravascular device between the first and second connection pieces in a direction transverse to a longitudinal axis of the intravascular device, and wherein in the closed position the at least one electrical contact is electrically coupled to the at least one electrical connector of the intravascular device received between the first and second connection pieces and a communication cable extends from the connector in a direction coaxial with or parallel to the longitudinal axis of the intravascular device.

In some embodiments, the connector includes a bias element urging the first and second connection pieces towards the closed position. The bias element can include a spring. The first connection piece can include a recess sized and shaped to receive a portion of the intravascular device that includes the at least one electrical connector. The at least one electrical contact can be secured to the second connection piece. The at least one electronic component can include a pressure sensing component and/or a flow sensing component. The at least one electronic component can also include an intravascular imaging component, such as an ultrasound transducer and/or an optical coherence tomography element. The second connection piece can be translatable relative to the first connection piece. The at least one electrical contact can be secured to the second connection piece such that the at least one electrical contact is spaced from a recess of the first connection piece in the open position and extends across the recess of the first connection piece in the closed position. The at least one electrical contact can include a split open comb electrical contact, a contact pad, and/or other suitable electrical contact(s). The second connection piece can be rotatable relative to the first connection piece. An axis of rotation of the second connection piece about the first connection piece can extend coaxial with or parallel to the longitudinal axis of the intravascular device when the intravascular device is received between the first and second connection pieces. The second connection piece can be pivotable relative to the first connection piece. A pivot axis of the second connection relative to the first connection piece can extend perpendicular to the longitudinal axis of the intravascular device when the intravascular device is received between the first and second connection pieces.

In some embodiments, a connector for an intravascular system is provided. The connector can include a first connection piece, a second connection piece, wherein the second connection piece is movable relative to the first connection piece between an open position and a closed position, and at least one electrical contact configured to interface with at least one electrical connector of an intravascular device, wherein in the open position an elongated opening is formed between the first and second connection pieces to facilitate insertion of the at least one electrical connector of the intravascular device between the first and second connection pieces in a direction transverse to a longitudinal axis of the intravascular device, and wherein in the closed position the at least one electrical contact is electrically coupled to the at least one electrical connector of the intravascular device received between the first and second connection pieces and a communication cable extends from the connector in a direction coaxial with or parallel to the longitudinal axis of the intravascular device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3 is a diagrammatic side view of a proximal connector portion of an intravascular device according to the present disclosure.

FIG. 4 is a diagrammatic side view of a proximal connector portion of an intravascular device similar to that of FIG. 3, but illustrating another aspect of the present disclosure.

FIG. 6*a* is a diagrammatic top view of the intravascular system of FIGS. 1 and 5, but showing the connector in a closed position according to the present disclosure.

FIG. 6*b* is a diagrammatic side view of the intravascular system of FIGS. 1, 5, and 6*a*, showing the connector in the closed position according to the present disclosure.

FIG. 14 is a diagrammatic cross-sectional end view of the intravascular system of FIGS. 12 and 13 taken along section line 14-14 of FIG. 13 and showing the connector in the closed position according to the present disclosure.

DETAILED DESCRIPTION

Figure 1:
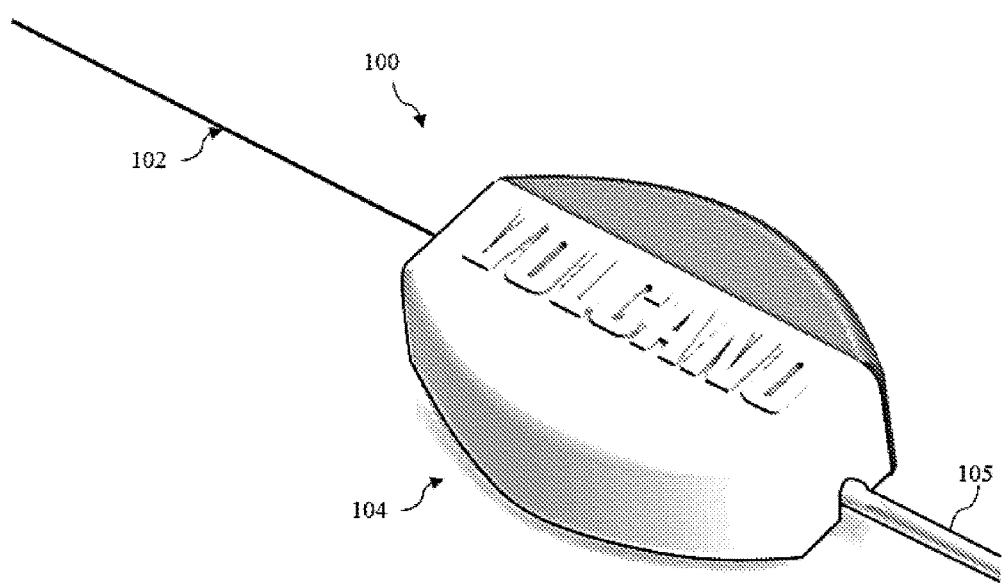
FIG. 1 is a diagrammatic perspective view of an intravascular system according to the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, intravascular catheters and intravascular guidewires. In that regard, intravascular catheters may or may not include a lumen extending along its length for receiving and/or guiding other instruments. If the intravascular catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an fro electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized. Further, in some instances the flexible elongate member includes multiple electronic, optical, and/or electro-optical components (e.g., pressure sensors, temperature sensors, imaging elements, optical fibers, ultrasound transducers, reflectors, mirrors, prisms, ablation elements, rf electrodes, conductors, etc.).

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring initially to FIG. 1, shown therein is an intravascular system 100 according to an embodiment of the present disclosure. In that regard, the intravascular system includes an intravascular device 102 and a connector 104. As will be discussed in greater detail below, a communication cable 105 extends from the connector 104 in a direction coaxial with or parallel to the longitudinal axis of the intravascular device 102. As a result of the communication cable 105 extending coaxial with or parallel to the intravascular device, the connector 104 and communication cable 105 are less likely to catch on a patient, patient's clothing, medical equipment (including tubes, catheters, wires, leads, etc.) and/or other structures in the procedure room when maneuvering the intravascular device 102.

Figure 2:
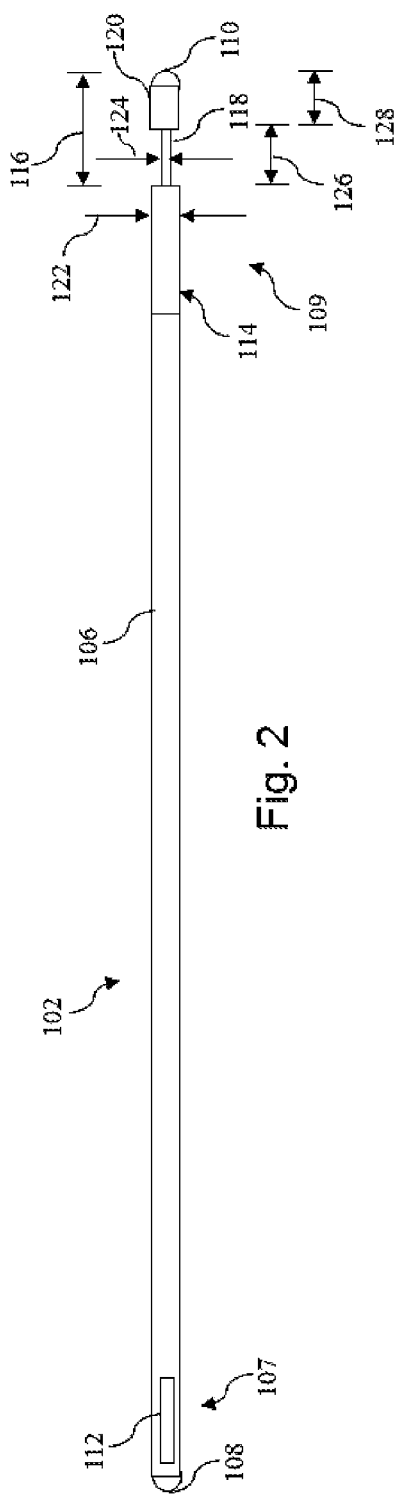
FIG. 2 is a diagrammatic side view of an intravascular device of the intravascular system of FIG. 1 according to the present disclosure.

Referring now to FIG. 2, a side view of the intravascular device 102 is provided according to an embodiment of the present disclosure. As shown, the intravascular device 102 includes a flexible elongate member 106 having a distal portion 107 adjacent a distal end 108 and a proximal portion 109 adjacent a proximal end 110. A component 112 is positioned within the distal portion 107 of the flexible elongate member 106 proximal of the distal tip 108. Generally, the component 112 is representative of one or more electronic, optical, or electro-optical components. In that regard, the component 112 can include a pressure sensor, a temperature sensor, an imaging element, an optical fiber, an ultrasound transducer, a reflector, a mirror, a prism, an ablation element, an rf electrode, a conductor, and/or combinations thereof. The specific type of component or combination of components can be selected based on an intended use of the intravascular device. In some instances, the component 112 is positioned less than 10 cm, less than 5, or less than 3 cm from the distal tip 108. In some instances, the component 112 is positioned within a housing of the intravascular device 102. In that regard, the housing can be a separate component secured to the flexible elongate member 106 in some instances. In other instances, the housing can be integrally formed as a part of the flexible elongate member 106.

The intravascular device 102 also includes a connection portion 114 adjacent the proximal portion 109 of the device. In that regard, the connection portion 114 can be spaced from the proximal end 110 of the flexible elongate member 106 by a distance 116. Generally, the distance 116 is between 0% and 50% of the total length of the flexible elongate member 106. While the total length of the flexible elongate member can be any length, in some embodiments the total length is between about 1300 mm and about 4000 mm, with some specific embodiments having a length of 1400 mm, 1900 mm, and 3000 mm. In some instances the connection portion 114 is spaced from the proximal end 110 between about 0 mm and about 1400 mm. In some specific embodiments, the connection portion 114 is spaced from the proximal end by a distance of 0 mm, 300 mm, and 1400 mm. Accordingly, in some instances the connection portion 114 is positioned at the proximal end 110. In some such embodiments, one or more aspects of the engagement and alignment features of the intravascular device 102 discussed below are positioned distal of the of the connection portion 114 instead of proximal of the connection portion 114 as shown in the embodiment of FIG. 2, or the engagement and alignment features may be omitted entirely.

In the illustrated embodiment of FIG. 2 the intravascular device 102 includes a section 118 extending proximally from the connection portion 114 to another section 120 that extends to proximal end 110. In the illustrated embodiment, the section 120 is rounded to proximal end 110. In other embodiments, the section 120 has a tapered, arcuate, and/or other changing profile as it extends proximally to proximal end 110. In that regard, in some instances the outer profile and/or diameter of the section 120 reduces as it extends proximally to proximal end 110 such that the reduced profile and/or diameter of the proximal end facilitates easier introduction of one or more other instruments over the intravascular device. In other embodiments, the section 120 has a constant profile as it extends proximally to proximal end 110.

As shown, the connection portion 114 has a diameter 122 (or other similar measurement for outer cross-section profiles for non-circular cross-sectional embodiments) while section 118 has a diameter 124 (again, or other similar measurement for outer cross-section profiles for non-circular cross-sectional embodiments). The diameter 124 of section 118 is different than the diameter 122 of connection portion 114. In that regard, the different sizes of the diameters 122, 124 create a structure that is configured to facilitate alignment and/or connection of the intravascular device 102 to a connector, such as connector 104. In the illustrated embodiment, the diameter 124 of section 118 is less than the diameter 122 of the connection portion 114. In some embodiments, the diameter 124 of section 118 is between about 40% and about 80% of diameter 122, with some particular embodiments being about 42%, 64%, and/or other percentage of diameter 122. In that regard, in some embodiments the diameter 122 of connection portion 114 is between about 0.0178 mm and about 3.0 mm, with some particular embodiments being 0.3556 mm (0.014") and 0.4572 mm (0.018"). Accordingly, in some embodiments the diameter 124 of section 118 is between about 0.007 mm and about 2.4 mm, with some particular embodiments being 0.15 mm, 0.19 mm, 0.23 mm, and 0.29 mm. In the illustrated embodiment, section 120 has a diameter that is approximately equal to diameter 122 and, therefore, greater than diameter 124. However, in other embodiments, section 120 has a diameter that is greater than diameter 122, less than diameter 122, greater than diameter 124, equal to diameter 124, and/or less than diameter 124. In some embodiments, section 118 is a section of a core wire extending through the connection portion 114.

As shown in FIG. 2, the section 118 extends proximally from connection portion 114 a distance 126, while section 120 extends proximally from section 118 to proximal end 110 a distance 128. Together, distances 126 and 128 equal the distance 116 that the connection portion 114 is spaced from the proximal end 110 of the intravascular device 102. In some instances, the distance 126 of is between about 0.508 mm (0.020") and about 2.54 mm (0.10"), with some particular embodiments being 0.762 mm (0.030"), 1.016 mm (0.040"), and 1.524 mm (0.060"). Further, while the transition between connection portion 114 and section 118 and the transition between section 118 and section 120 are shown as being stepped in the illustrated embodiments, in other embodiments the transitions are tapered and/or otherwise make a gradual change in outer diameter along the length of the intravascular device. In some embodiments, use of tapered and/or gradual transitions results in the proximal portion of the intravascular device 102 not having any sharp edges. In some implementations, the use of tapered and/or gradual transitions for one or both of the transitions between section 118 and either the connection portion 114 or section 120 makes cleaning the proximal portion of the device (e.g., to remove any liquids or other unwanted materials on the surface of the proximal portion of the intravascular device) easier.

The connection portion 114 is configured to facilitate communication between the intravascular device 102 and another device. More specifically, in some embodiments the connection portion 114 is configured to facilitate communication of data obtained by the component 112 to another device, such as a computing device or processor. Accordingly, in some embodiments the connection portion 114 is an electrical connector. In such instances, the connection portion 114 can be configured to provide an electrical connection to one or more electrical conductors that extend along the length of the flexible elongate member 106 and are electrically coupled to the component 112. For example, the connection portion 114 can include conductive bands, rings, coatings, coils, etc. In some instances, the connection portion 114 includes one or more electrical connectors as described in U.S. patent application Ser. No. 13/931,052, titled "INTRAVASCULAR DEVICES, SYSTEMS, AND METHODS," filed Jun. 28, 2013, which is hereby incorporated by reference in its entirety. In other embodiments, the connection portion 114 includes an optical connector. In such instances, the connection portion 114 provides an optical connection to one or more optical communication pathways (e.g., fiber optic cable) that extend along the length of the flexible elongate member 106 and are optically coupled to the component 112. Further, in some embodiments the connection portion 114 provides both electrical and optical connections to both electrical conductor(s) and optical communication pathway(s) coupled to the component 112. In that regard, it should again be noted that component 112 can be comprised of a plurality of elements in some instances. In some instances, the connection portion 114 can be configured to provide a physical connection to another device, either directly or indirectly. In other instances, the connection portion 114 can be configured to facilitate wireless communication between the intravascular device 102 and another device. Generally, any current or future developed wireless protocol(s) may be utilized. In yet other instances, the connection portion 114 facilitates both physical and wireless connection to another device.

As noted above, in some instances the connection portion 114 provides a connection between the component 112 of the intravascular device 102 and an external device. Accordingly, in some embodiments one or more electrical conductors, one or more optical pathways, and/or combinations thereof extend along the length of the flexible elongate member 106 between the connection portion 114 and the component 112 to facilitate communication between the connection portion 114 and the component 112. Generally, any number of electrical conductors, optical pathways, and/or or combinations thereof can extend along the length of the flexible elongate member 106 between the connection portion 114 and the component 112. In some instances, between one and ten electrical conductors and/or optical pathways extend along the length of the flexible elongate member 106 between the connection portion 114 and the component 112. For the sake of clarity and simplicity, the embodiments of the present disclosure described below include three electrical conductors and, therefore, the connection portion 114 is described as having three separate electrical connections corresponding to the three electrical conductors.

For example, as shown in FIG. 3, in some instances the connection portion 114 includes conductive portions 132, 134, and 136 that are separated from one another and the main body of the flexible elongate member 106 by insulating portions 138, 140, 142, and 144. In that regard, the conductive portions 132, 134, and 136 are formed of a conductive material and are portions of a hypotube, a coil, conductive coating formed over a tubular member, and/or combinations thereof in some instances. It is understood that the total number of communication pathways and/or the number of electrical conductors and/or optical pathways is different in other embodiments and, therefore, the number of conductive portions (or optical connectors) included in connection portion is different as well. More specifically, the number of communication pathways and the number of electrical conductors and optical pathways extending along the length of the flexible elongate member 106 can be selected based on the desired functionality of the component 112 and the corresponding elements that define component 112 to provide such functionality. As a result, the number and type of connections provided by connection portion 114 are likewise determined by the desired functionality of the component 112, the corresponding elements that define component 112 to provide such functionality, and the communication needs for such elements. Further still, in some instances, one or more of the insulating portions 138, 140, 142, and 144 is omitted. For example, as shown in the exemplary embodiment of FIG. 4, insulating portion 144 has been omitted.

Figure 5:
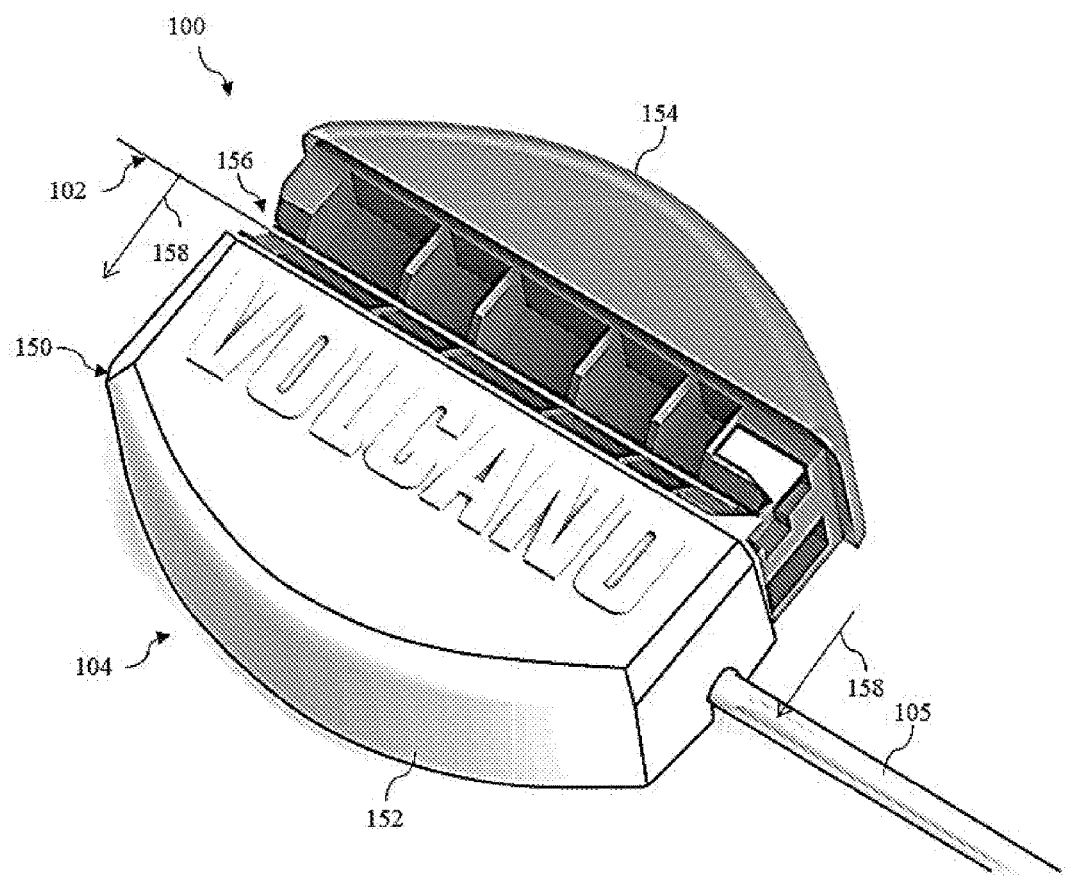
FIG. 5 is a diagrammatic perspective top view of the intravascular system of FIG. 1 showing the connector in an open position according to the present disclosure.

Referring now to FIGS. 5, 6a, and 6b, shown therein are additional details of the connector 104. In that regard, FIG. 5 is a diagrammatic perspective top view of the intravascular system 100 showing the connector 104 in an open position; FIG. 6a is a diagrammatic top view of the intravascular system 100 showing the connector 104 in a closed position; and FIG. 6b is a diagrammatic side view of the intravascular system 100 showing the connector 104 in the closed position. In some instances, the connectors of the present application incorporate one or more features of the connectors described in U.S. patent application Ser. No. 13/930,787, titled "SIDE-LOADING CONNECTORS FOR USE WITH INTRAVASCULAR DEVICES AND ASSOCIATED SYSTEMS AND METHODS" and filed Jun. 28, 2013, which is hereby incorporated by reference in its entirety. In that regard, connector 104 is configured to interface with the connection portion 114 of the intravascular device 102 to facilitate communication between the intravascular device 102 and a separate component, such as a patient interface module (PIM) and/or a processing system. In particular, the connector 104 is configured to facilitate communication between one or more electronic components of the intravascular device 102 that are electrically coupled to the connection portion 114 and a separate component, such as a patient interface module (PIM) and/or a processing system associated with the one or more electronic components.

As shown in FIG. 5, the connector 104 includes a component 152 and a component 154. In the illustrated embodiment, the component 152 is movable with respect to the component 154. In particular, the components 152 and 154 are slidable with respect to one another to facilitate insertion of an intravascular device into the connector 104 and subsequent engagement of the connector with the received intravascular device that results in one or more electrical connections between the intravascular device and the connector. In the illustrated embodiment, the component 152 includes an upper surface with a gripping feature illustrated as raised letters spelling "VOLCANO". In that regard, the gripping feature is generally representative of any type of structure (e.g., projection(s), recess(es), combinations thereof, etc.), texture (e.g., roughened, knurled, patterned, combinations thereof, etc.) and/or combinations thereof configured to provide an interface to assist a user in translating the component 152 relative to the component 154 or vice versa.

As shown in FIG. 5, the component 154 includes a recess 156 that is sized and shaped to receive an intravascular device. In particular, the recess 156 is sized and shaped to receive a connection portion of the intravascular device. In some instances, the recess 156 includes features as described in U.S. patent application Ser. No. 13/930,787, titled "SIDE-LOADING CONNECTORS FOR USE WITH INTRAVASCULAR DEVICES AND ASSOCIATED SYSTEMS AND METHODS" and filed Jun. 28, 2013 and/or U.S. patent application Ser. No. 13/930,636, titled "SIDE-LOADING CONNECTORS FOR USE WITH INTRAVASCULAR DEVICES AND ASSOCIATED SYSTEMS AND METHODS" and filed Jun. 28, 2013, each of which is hereby incorporated by reference in its entirety.

To help ensure that the connection portion of the intravascular device is properly aligned with the electrical contacts of the connector 104, the one or both of the components 152, 154 may include one or more visual markers (active and/or passive) and/or be at least partially formed of a clear or translucent material. Alignment of the intravascular device 102 with respect to the connector 104 can also facilitate use of one or more wiping elements to remove liquid on the surface of the intravascular device 102 that can cause bridging between adjacent conductors. In that regard, the component(s) 152, 154 may include one or more visual markers and/or structural components to facilitate alignment as well as one or more wiping elements as described in U.S. patent application Ser. No. 13/930,787, titled "SIDE-LOADING CONNECTORS FOR USE WITH INTRAVASCULAR DEVICES AND ASSOCIATED SYSTEMS AND METHODS" and filed Jun. 28, 2013 and/or U.S. patent application Ser. No. 13/930,636, titled "SIDE-LOADING CONNECTORS FOR USE WITH INTRAVASCULAR DEVICES AND ASSOCIATED SYSTEMS AND METHODS" and filed Jun. 28, 2013, each of which is hereby incorporated by reference in its entirety.

To guide the movement of the component 152 with respect to the component 154, in some embodiments one or both of the components 152, 154 includes projections that are received within corresponding slots or openings of the other component 154, 152, respectively. In that regard, the slots or openings generally extend along the length of the component(s) in a direction parallel to the longitudinal axis of the component. The projections extend from the component(s) in a manner such that when the components 152, 154 are assembled together the projections are received within the openings of the other component. In that regard, the projections can be sized and shaped to be slidably received within the openings such that the projections can translate along the length of the openings when the component 152 is translated relative to the component 154. In some instances, the opposing ends of the openings serve as stops to limit travel of the component 152 relative to the component 154. In that regard, the projection(s) will contact a first end of the opening when the component 152 is in the fully opened position and will contact a second end of the opening opposite the first end when the component 152 is in the fully closed position. In some embodiments, the connector 104 includes a bias element, such as a spring, to lightly lock the mechanism in the closed position. In that regard, the bias element can bias the component 152 of the connector 104 toward the closed position through at least part of the sliding motion between the components 152, 154.

The component 152 includes electrical contacts configured to engage corresponding electrical contacts of an intravascular device, such as conductive portions 132, 134, and 136 of connection portion 114 of the intravascular device 102. It is understood that any arrangement of electrical connection between the connector 104 and an intravascular device may be utilized. In that regard, the connector 104 may include any number of electrical contacts (e.g., 1, 2, 3, 4, 5, 6, 7, 8, or more electrical contacts), may include a single contact for each of one or more conductive portions of the intravascular device, may include multiple contacts for each of one or more conductive portions of the intravascular device, and/or combinations thereof. Further, the component 152 can include any suitable type of electrical contact(s), including without limitation split, open-comb electrical contacts, contact pads, contact rings, contact springs, and/or combinations thereof. In some implementations, the electrical contact(s) are configured to allow rotation of the intravascular device 102 while maintaining electrical connection.

Collectively FIGS. 5, 6a, and 6b illustrate a transition of the connector 104 from the open position (FIG. 5) to the closed position (FIGS. 6a and 6b). As shown in FIG. 5, the connector 104 is configured to receive the intravascular device 102 in a side-loading fashion. More specifically, the recess 156 in the component 154 is revealed when the component 152 is retracted to the open position such that the intravascular device 102 can be seated within the recess 156 by moving the intravascular device 102 in a direction transverse to its longitudinal axis. To load the intravascular device within the connector 104, the connector 104 may be moved relative to the intravascular device 102, the intravascular device 102 may be moved relative to the connector 104, and/or combinations thereof. In some instances, with the intravascular device 102 positioned within the 156 of the component 154, the intravascular device 102 is moved to engage section 120 with an outer surface of component 154 to properly align the intravascular device relative to the component 154 while in the open position. In other instances, the intravascular device 102 is not moved to engage section 120 with an outer surface of the component 154 until after transitioning the component 152 to the closed position.

With the intravascular device 102 positioned within the recess 156 of component 154, the component 154 is translated with respect to the component 152, as indicated by arrow 158 in FIG. 5, to the closed position illustrated in FIGS. 6a and 6b. As noted above, in some implementations the connector 104 is biased towards the closed position by a biasing element. In the closed position, the intravascular device 102 is held between the components 152 and 154 such that the connector 104 is in electrical communication with the connection portion 114 of the intravascular device. In particular, in the closed position the electrical contacts of the component 152 engage the connection portion 114 of the intravascular device 102. To disconnect and remove the intravascular device 102 from the connector 104, the component 154 is translated with respect to the component 152 in the opposite direction back to the open position of FIG. 5.

As noted above, the connector 104 is configured to interface with a connection portion of an intravascular device to facilitate communication between the intravascular device and a separate component. To that end, the communication cable 105 that is configured to carry signals between the connector 104 and the separate component. In particular, the communication cable 105 is configured to carry electrical signals and includes one or more electrical conductors extending along its length to facilitate such electrical communication. However, the type of communication cable utilized is dependent on the type of electronic, optical, and/or electro-optical components that are incorporated into the intravascular device. In that regard, the communication cable 105 may include one or more of an electrical conductor, an optical fiber, and/or combinations thereof. In some instances, the communication cable 105 is configured to be plugged into an interface of a processing system. In that regard, the interface is a patient interface module (PIM) in some instances.

As shown in FIGS. 6a and 6b, the communication cable 105 extends from the component 152 such that a longitudinal axis 162 of the communication cable 105 is coaxial with or parallel to a longitudinal axis 160 of the intravascular device 102 received within the connector. In the illustrated embodiment of FIGS. 6a and 6b, the communication cable 105 extends parallel to the intravascular device 102 engaged by connector 104. In particular, FIG. 6a illustrates that the longitudinal axis 162 of the communication cable 105 is aligned with respect to the longitudinal axis 160 of the intravascular device 102 when viewed from the top, but FIG. 6b illustrates that the longitudinal axis 162 of the communication cable 105 is offset with respect to the longitudinal axis 160 of the intravascular device 102 by a distance 164 when view from the side (or end). Accordingly, in the illustrated embodiment the communication cable 105 may be considered aligned with the intravascular device 102 in the horizontal direction and offset in the vertical direction. In other instances, the communication cable 105 is coaxial with the intravascular device 102. In yet other instances, the communication cable 105 extends parallel to the intravascular device 102, but is offset with respect to the intravascular device in both vertical and horizontal directions.

As a result of the communication cable 105 extending coaxial with or parallel to the intravascular device, the bending moment of the connection between the connector 104 and the intravascular device 102 is greatly reduced. In particular, the connector 104 and the communication cable 105 are less likely to catch on a patient, patient's clothing, medical equipment (including tubes, catheters, wires, leads, etc.) and/or other structures in the procedure room when maneuvering the intravascular device 102 during a procedure as compared to a connector and/or communication cable that extend in a direction perpendicular to the intravascular device. Accordingly, the connectors of the present disclosure provide a better user experience for the medical professional, improve maneuverability of the intravascular device while coupled to the connector, and lower the likelihood of damage to the intravascular device and/or connector during a procedure, all of which improve patient safety and treatment outcomes.

Figure 7:
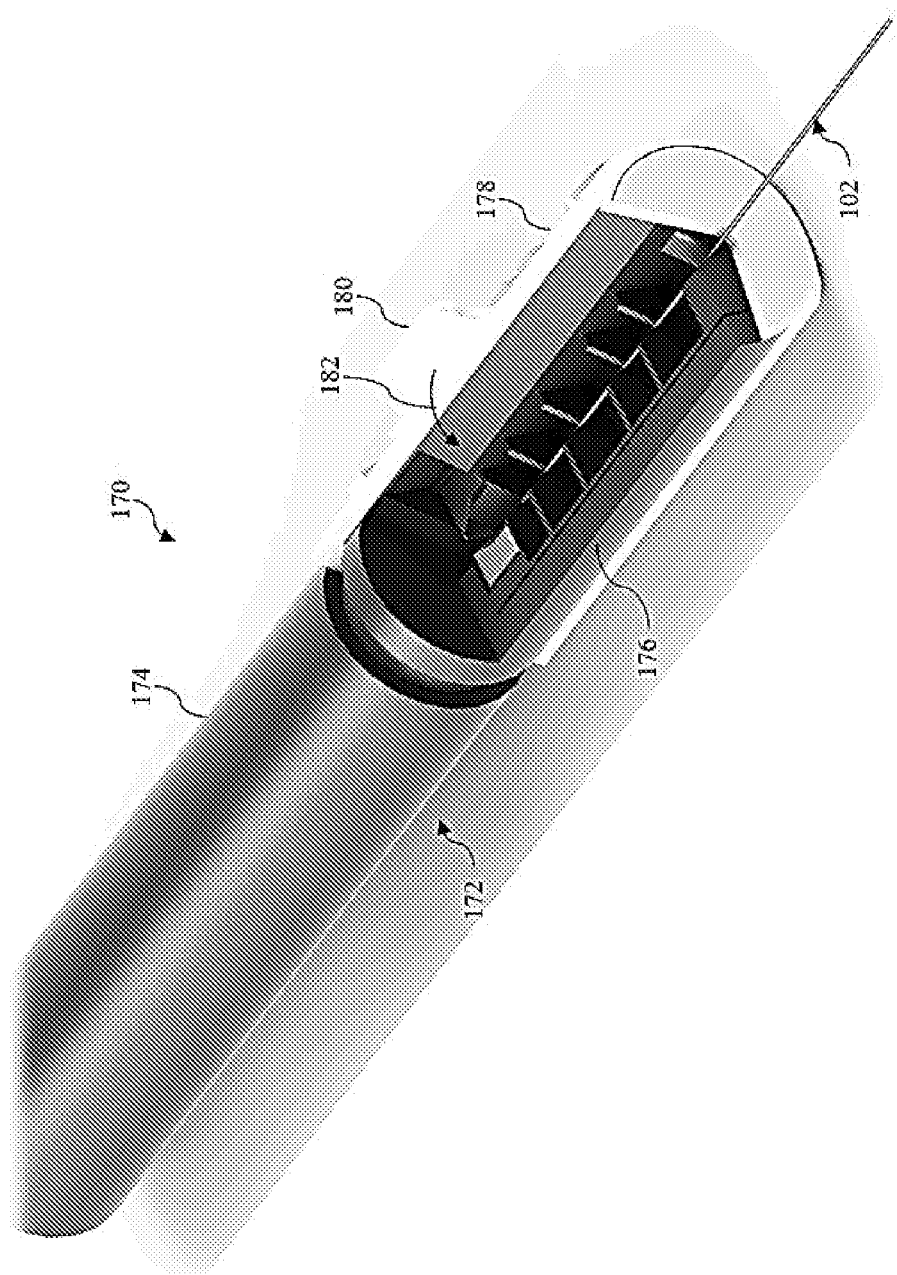
FIG. 7 is a diagrammatic perspective top view of an intravascular system showing a connector in an open position according to the present disclosure.
Figure 8:
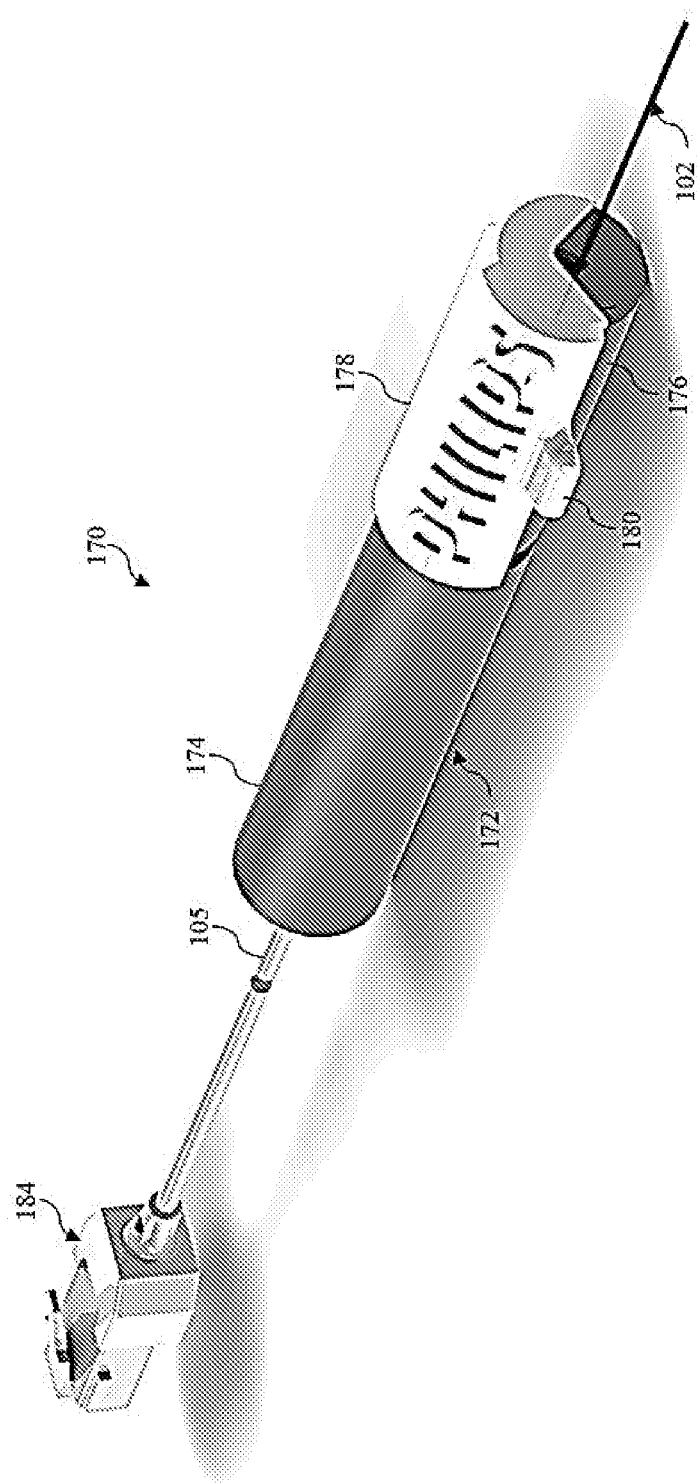
FIG. 8 is a diagrammatic perspective top view of the intravascular system of FIG. 7, but showing the connector in the closed position according to the present disclosure.

Referring now to FIGS. 7-14, shown therein are aspects of intravascular systems incorporating alternative connectors in accordance with the present disclosure. Referring to FIGS. 7 and 8, shown therein are aspects of an intravascular system 170 having an intravascular device 102 and a connector 172 according to the present disclosure. In that regard, connector 172 can include many features similar to those described above with respect to connector 104. Accordingly, the following description will focus on features of connector 172 that are different than those of connector 104. However, it is understood that the various features of both connectors 104 and 172 may be combined in any of a variety of manners consistent with the present disclosure. In that regard, unless otherwise noted, it should be presumed that any feature of connector 104 may be implemented within connector 172 and vice versa.

As shown in FIG. 7, the connector 172 includes a handle 174 for grasping by a user. The handle is coupled to and/or integrally formed with a component 176 that includes a recess sized and shaped to receive the intravascular device 102. The connector 172 also includes a component 178 that is movable with respect to the component 176. In particular, the component 178 is rotatable with respect to the component 176 to facilitate insertion of an intravascular device into the connector 172 and subsequent engagement of the connector with the received intravascular device that results in one or more electrical connections between the intravascular device and the connector. The axis of rotation of the component 178 relative to the component 176 can be coaxial or parallel to a longitudinal axis of the handle 174 and/or the longitudinal axis of an intravascular device received within the connector 172.

The component 178 can include a gripping feature 180 to facilitate rotation of the component 178 relative to the component 176. In the illustrated embodiment the gripping feature 180 is a tab or projection configured to allow a user's thumb or finger to actuate rotation of the component 178 with respect to the component 176. In that regard, the gripping feature 180 is generally representative of any type of structure (e.g., projection(s), recess(es), combinations thereof, etc.), texture (e.g., roughened, knurled, patterned, combinations thereof, etc.) and/or combinations thereof configured to provide an interface to assist a user in rotating the component 178 relative to the component 176.

The component 178 includes electrical contacts configured to engage corresponding electrical contacts of an intravascular device, such as conductive portions 132, 134, and 136 of connection portion 114 of the intravascular device 102. Accordingly, when the component 178 is rotated from the open position (FIG. 7) to the closed position (FIG. 8), as indicated by arrow 182, the electrical contacts of component 178 will engage corresponding electrical contacts of the intravascular device 102 received within component 176 to create a communication pathway. As noted above, the connector 172 is configured to interface with a connection portion of an intravascular device to facilitate communication between the intravascular device and a separate component. To that end, as shown in FIG. 8, the communication cable 105 extends from the handle 174 such that the communication cable 105 is coaxial with or parallel to the intravascular device 102 received within the connector 172.

Figure 9:
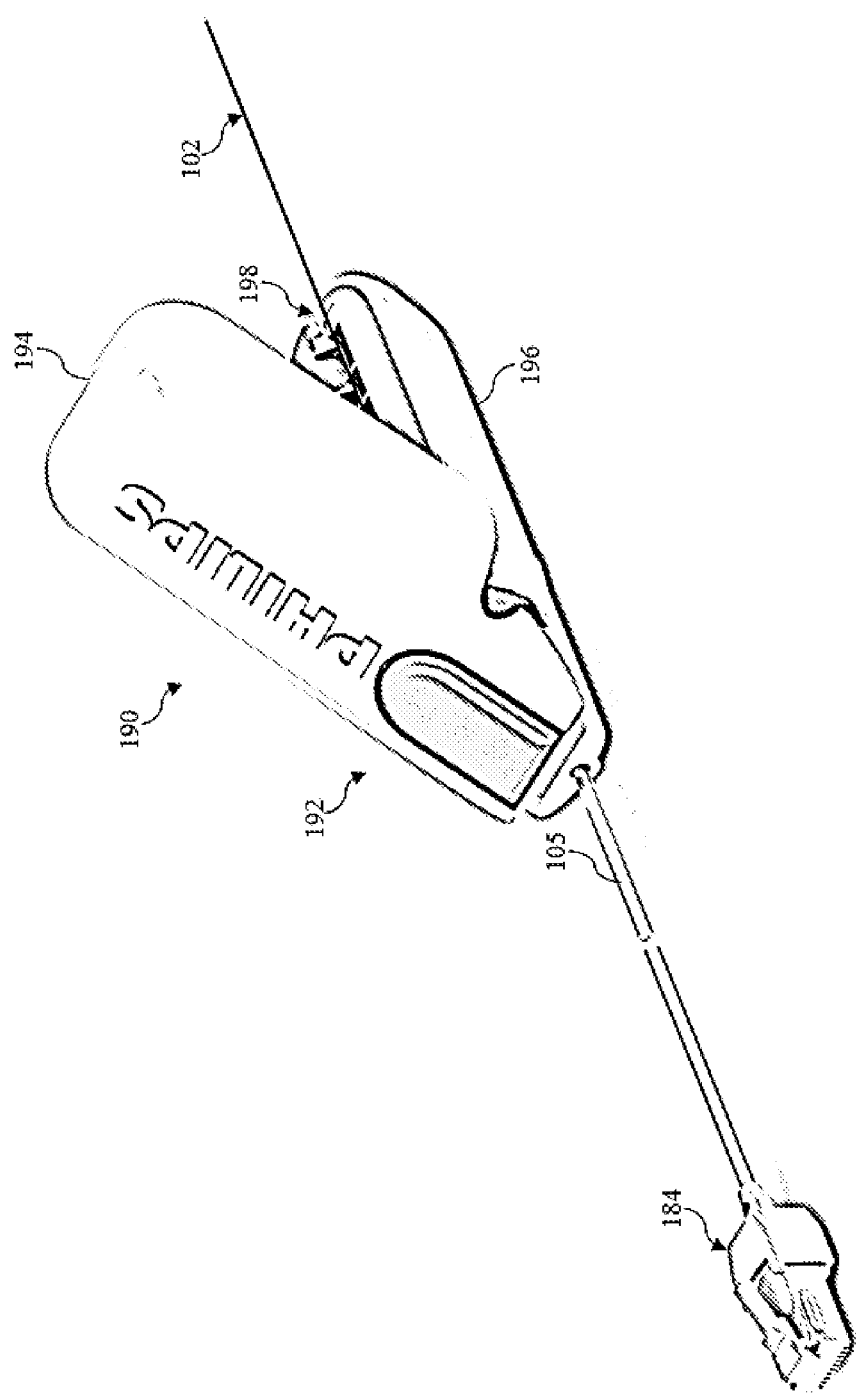
FIG. 9 is a diagrammatic perspective top view of an intravascular system showing a connector in an open position according to the present disclosure.
Figure 10:
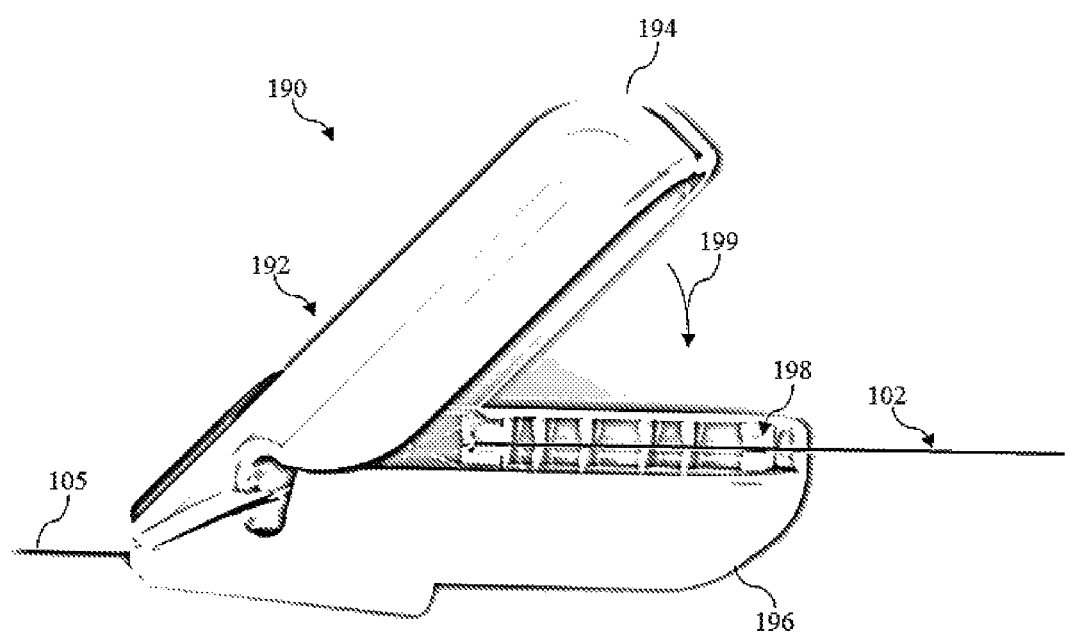
FIG. 10 is a diagrammatic perspective side view of the intravascular system of FIG. 9 showing the connector in the open position according to the present disclosure.
Figure 11:
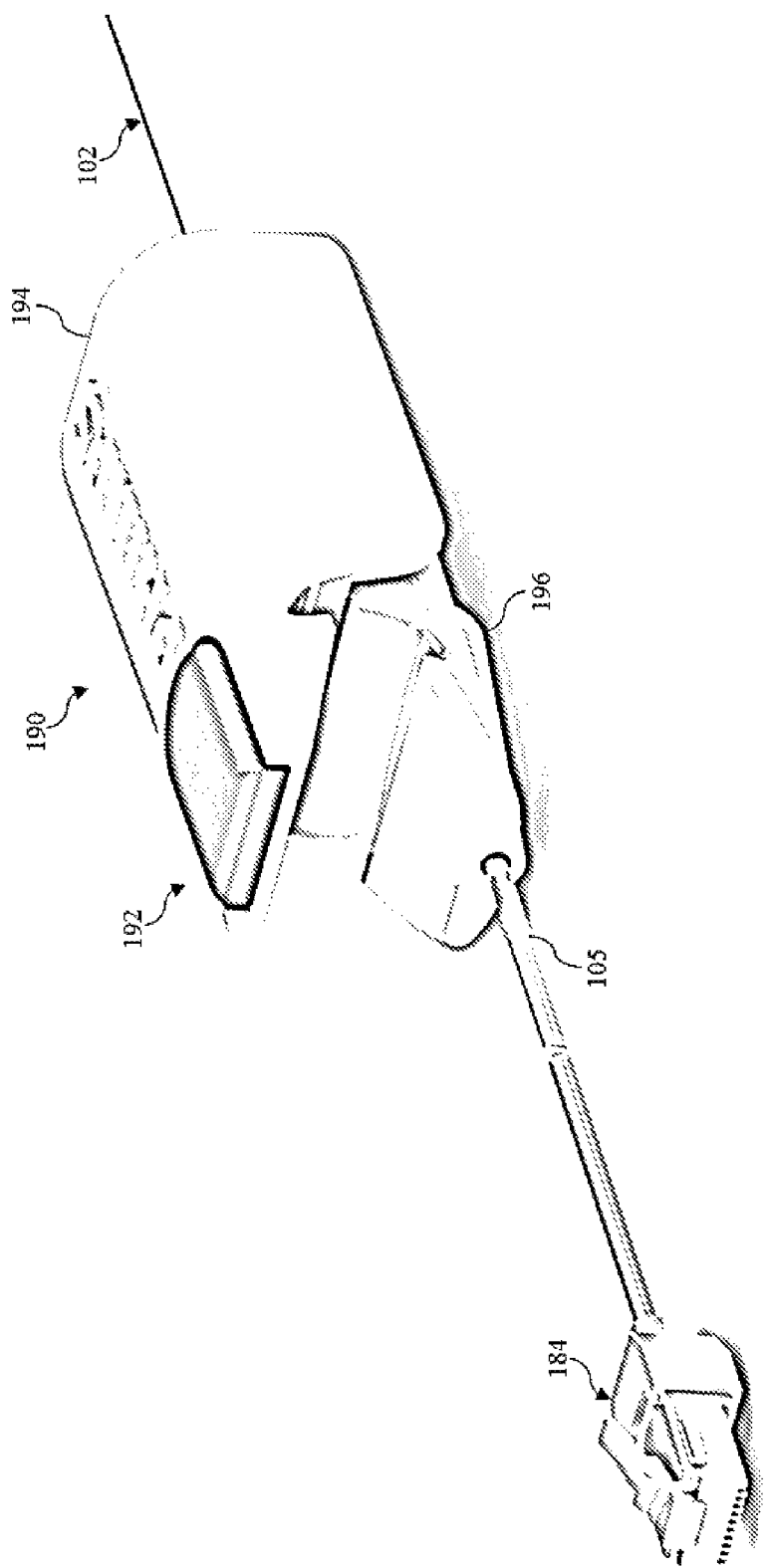
FIG. 11 is a diagrammatic perspective top view of the intravascular system of FIGS. 9 and 10, but showing the connector in the closed position according to the present disclosure.

Referring to FIGS. 9-11, shown therein are aspects of an intravascular system 190 having an intravascular device 102 and a connector 192 according to the present disclosure. In that regard, connector 192 can include many features similar to those described above with respect to connectors 104 and 172. Accordingly, the following description will focus on features of connector 192 that are different than those of connectors 104 and 172. However, it is understood that the various features of connectors 104, 172, and 192 may be combined in any of a variety of manners consistent with the present disclosure. In that regard, unless otherwise noted, it should be presumed that any feature of connectors 104, 172, and 192 may be implemented within the other connectors and vice versa.

As shown in FIG. 9, the connector 192 includes a component 194 and a component 196. The component 196 includes a recess 198 sized and shaped to receive the intravascular device 102. The component 194 is movable with respect to the component 196. In particular, the component 194 is pivotable with respect to the component 196 to facilitate insertion of an intravascular device into the connector 192 and subsequent engagement of the connector with the received intravascular device that results in one or more electrical connections between the intravascular device and the connector. The pivot axis of the component 194 relative to the component 196 can be perpendicular to a longitudinal axis of the component 196 and/or the longitudinal axis of an intravascular device received within the connector 192.

The component 194 includes electrical contacts configured to engage corresponding electrical contacts of an intravascular device, such as conductive portions 132, 134, and 136 of connection portion 114 of the intravascular device 102. Accordingly, when the component 178 is pivoted from the open position (FIGS. 9 and 10) to the closed position (FIG. 11), as indicated by arrow 199, the electrical contacts of component 194 will engage corresponding electrical contacts of the intravascular device 102 received within component 196 to create a communication pathway. In some instances, the connector 192 is biased towards the closed position of FIG. 11. For example, a bias element, such as a spring, can urge the components 194 and 196 towards the closed position. As noted above, the connector 192 is configured to interface with a connection portion of an intravascular device to facilitate communication between the intravascular device and a separate component. To that end, as shown in FIG. 9-11, the communication cable 105 extends from the connector 192 such that the communication cable 105 is coaxial with or parallel to the intravascular device 102 received within the connector 192.

Figure 12:
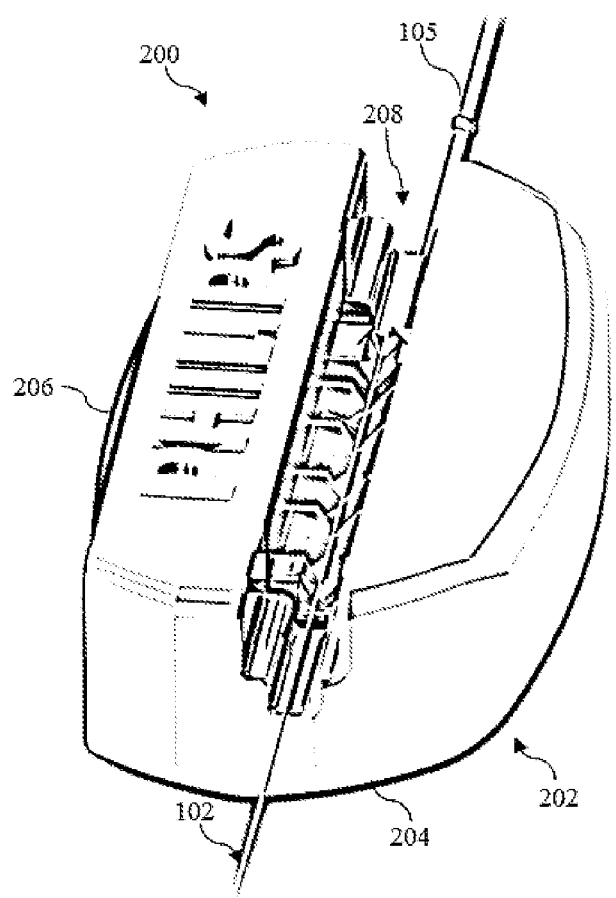
FIG. 12 is a diagrammatic perspective top view of an intravascular system showing a connector in an open position according to the present disclosure.
Figure 13:
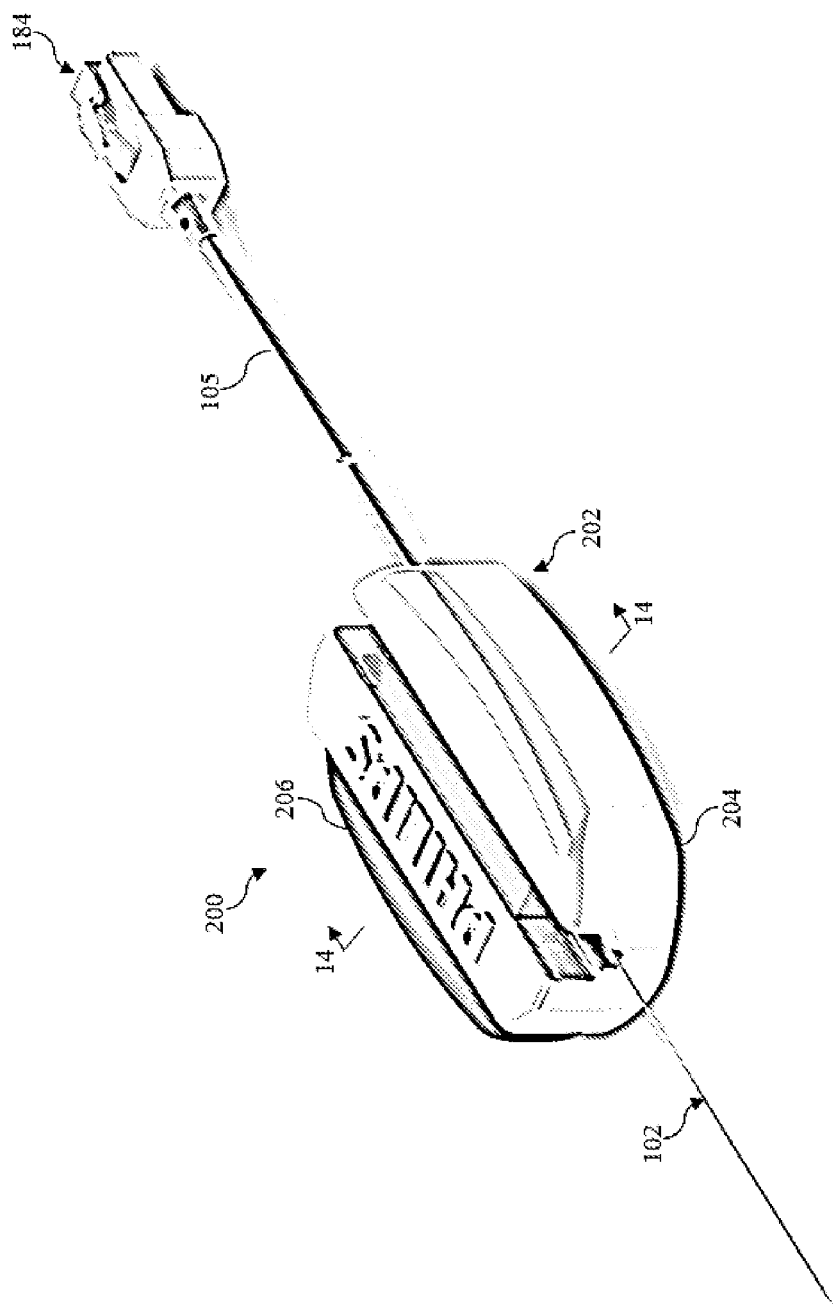
FIG. 13 is a diagrammatic perspective top view of the intravascular system of FIG. 12, but showing the connector in the closed position according to the present disclosure.

Referring to FIGS. 12-14, shown therein are aspects of an intravascular system 200 having an intravascular device 102 and a connector 202 according to the present disclosure. In that regard, connector 202 can include many features similar to those described above with respect to connectors 104, 172, and 192. Accordingly, the following description will focus on features of connector 202 that are different than those of connectors 104, 172, and 192. However, it is understood that the various features of connectors 104, 172, 192, and 202 may be combined in any of a variety of manners consistent with the present disclosure. In that regard, unless otherwise noted, it should be presumed that any feature of connectors 104, 172, 192, and 202 may be implemented within the other connectors and vice versa.

As shown in FIGS. 12-14, the connector 202 includes a component 204 and a component 206. The component 204 includes a recess 208 sized and shaped to receive the intravascular device 102. The component 206 is movable with respect to the component 204. In particular, the component 206 is slidable with respect to the component 204 to facilitate insertion of an intravascular device into the connector 202 and subsequent engagement of the connector with the received intravascular device that results in one or more electrical connections between the intravascular device and the connector. The sliding movement of the component 206 relative to the component 204 can be parallel to a longitudinal axis of the component 204 and/or the longitudinal axis of an intravascular device received within the connector 202.

The component 206 includes electrical contacts 210 configured to engage corresponding electrical contacts of an intravascular device, such as conductive portions 132, 134, and 136 of connection portion 114 of the intravascular device 102. In particular, as best shown in FIG. 14, the component 206 includes split, open-comb electrical contacts 210. In that regard, each of the electrical contacts 210 can be configured to receive a conductive portion of an intravascular device therein such that some of the teeth of the open-comb electrical contact will be positioned above the conductive portion and others of the teeth of the open-comb electrical contact will be positioned below the conductive portion. This arrangement provides a secure and reliable electrical connection between the electrical contact 210 of the connector 202 and the corresponding conductive portion of the intravascular device.

Further, the open-comb electrical contacts are particularly well-suited to facilitate proper electrical connection between the connector 202 and an intravascular device 102 positioned within the recess 208 of component 204 when the component 206 is translated relative to the component 204 from the open position towards the closed position. Further still, the open-comb configuration allows for the intravascular device to be rotated with respect to the connector while maintaining a proper electrical connection. Thus, the open-comb configuration allows a user (e.g., surgeon) to keep the connector 202 connected to the intravascular device while the intravascular device is moved or advanced through the vasculature with little resistance to rotational movement of the intravascular device. In other words, the intravascular device can be moved through the vasculature, undergoing various twists and turns, without the connector 202 needing to move with the rotations of the intravascular device. Also, the open-comb configuration helps ensure good electrical contact due to the multiple fingers for each of the contacts. In addition, the open end of the open-comb configuration provides a good guide for ensuring that the intravascular device is correctly positioned when the component 206 is closed. While various advantages of the open-comb configuration have been described, it is understood that any appropriately sized electrical contacts can be utilized, including a single contact or a plurality of contacts.

When the component 206 is translated from the open position (FIG. 12) to the closed position (FIGS. 13 and 14) the electrical contacts 210 of component 206 will engage corresponding electrical contacts of the intravascular device 102 received within component 204 to create a communication pathway. Further, a section 212 of the component 206 will extend over the recess 208 of component 204 to secure the intravascular device 102 within the connector 202 and protect the electrical connections from fluids and/or other potential contaminants that could damage or interfere with electrical communication. In some instances, the connector 192 is biased towards the closed position of FIG. 14. For example, a bias element 214, such as a spring, can urge the components 204 and 206 towards the closed position. Accordingly, to move the component 206 into the open position a user advances the component 206 against the bias element 214 in the direction of arrow 216. As shown in FIG. 12, in the open position the section 212 of component 206 is spaced from the recess 208 of component 204 such that an opening 218 in component 206 is positioned over the recess 208 to define a pathway into connector 202 for receiving the intravascular device 102. In this regard, referring to FIG. 14, in the open position section 212 of component 206 will be positioned under section 220 of component 204.

Again, the connector 202 is configured to interface with a connection portion of an intravascular device to facilitate communication between the intravascular device and a separate component. To that end, as shown in FIGS. 12 and 13, the communication cable 105 extends from the connector 202 such that the communication cable 105 is coaxial with or parallel to the intravascular device 102 received within the connector 202.

What is claimed is:

1. An intravascular system, comprising:
   an intravascular device having:
      a flexible elongate member having a proximal portion and a distal portion,
      at least one electronic component secured to the distal portion of the flexible elongate member, and
      at least one electrical connector secured to the proximal portion of the flexible elongate member, wherein the at least one electrical connector is electrically coupled to the at least one electronic component secured to the distal portion of the flexible elongate member; and
   a connector for coupling to the proximal portion of the flexible elongate member, the connector having:
      a first connection piece including a recess and a first opening,
      a second connection piece including a second opening, wherein the second connection piece is translatable relative to the first connection piece between an open position and a closed position,
      at least one electrical contact configured to interface with the at least one electrical connector of the intravascular device, and
      wherein in the open position, the first opening of the first connection piece is at least partially aligned with the second opening of the second connection piece to form a pathway to the recess of the first connection piece to facilitate insertion of the at least one electrical connector of the intravascular device into the recess of the first connection piece in a direction transverse to a longitudinal axis of the intravascular device, and
      wherein in the closed position, the second connection piece is positioned relative to the first connection piece such that the second opening of the second connection piece is offset from the first opening of the first connection piece to secure the at least one electrical connector of the intravascular device within the recess and couple the at least one electrical contact to the at least one electrical connector of the intravascular device.

2. The system of claim 1, wherein the connector further includes a bias element urging the first and second connection pieces towards the closed position.

3. The system of claim 1, wherein the recess is sized and shaped to receive a portion of the intravascular device that includes the at least one electrical connector.

4. The system of claim 3, wherein the at least one electrical contact is secured to the second connection piece.

5. The system of claim 1, wherein the at least one electronic component includes at least one of a pressure sensing component, a flow sensing component, or an intravascular imaging component.

6. The system of claim 1, wherein the at least one electrical contact is secured to the second connection piece such that the at least one electrical contact is spaced from the recess of the first connection piece in the open position and extends across the recess of the first connection piece in the closed position.

7. The system of claim 6, wherein the at least one electrical contact comprises a split open comb electrical contact.

8. The system of claim 2, wherein the bias element includes a spring.

9. The system of claim 2, wherein the bias element is positioned within a chamber in the first connection piece.

10. The system of claim 9, wherein the chamber comprises a first shape, and wherein the second connection piece comprises a member having a second shape corresponding to the first shape such that a portion of the member is received in the chamber in the open position.

11. The system of claim 1, further comprising a communication cable extending from the connector in a direction coaxial with or parallel to the longitudinal axis of the intravascular device.

12. The system of claim 1, wherein the first opening is aligned with the recess of the first connection piece.

13. A connector for an intravascular system, comprising:
a first connection piece including a recess and a first opening,
a second connection piece including a second opening, wherein the second connection piece is translatable relative to the first connection piece between an open position and a closed position,
at least one electrical contact configured to interface with at least one electrical connector of an intravascular device, and
wherein in the open position, the first opening of the first connection piece is at least partially aligned with the second opening of the second connection piece to form a pathway to the recess of the first connection piece to facilitate insertion of the at least one electrical connector of the intravascular device into the recess of the first connection piece in a direction transverse to a longitudinal axis of the intravascular device, and
wherein in the closed position, the second connection piece is positioned relative to the first connection piece such that the second opening of the second connection piece is offset from the first opening of the first connection piece to secure the at least one electrical connector of the intravascular device within the recess and couple the at least one electrical contact to the at least one electrical connector of the intravascular device.

14. The connector of claim 13, further comprising a bias element that urges the first and second connection pieces towards the closed position.

15. The connector of claim 13, wherein the recess is sized and shaped to receive a portion of an intravascular device that includes the at least one electrical connector.

16. The connector of claim 13, wherein the at least one electrical contact is secured to the second connection piece.

17. The connector of claim 13, wherein the at least one electrical contact is secured to the second connection piece such that the at least one electrical contact is spaced from the recess of the first connection piece in the open position and extends across the recess of the first connection piece in the closed position.

18. The connector of claim 13, wherein the at least one electrical contact comprises a split open comb electrical contact.

19. The connector of claim 13, wherein the bias element includes a spring.

20. The connector of claim 13, wherein the first opening is aligned with the recess of the first connection piece.

* * * * *